United States Patent
Mueller et al.

(10) Patent No.: US 10,278,769 B2
(45) Date of Patent: May 7, 2019

(54) SURGICAL INSTRUMENT WITH A SEPARABLE COAXIAL JOINT

(71) Applicant: COVIDIEN LP, Mansfield, MA (US)

(72) Inventors: Peter M. Mueller, Frederick, CO (US); Allan J. Evans, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 849 days.

(21) Appl. No.: 14/691,940

(22) Filed: Apr. 21, 2015

(65) Prior Publication Data
US 2015/0223871 A1    Aug. 13, 2015

Related U.S. Application Data

(62) Division of application No. 12/822,024, filed on Jun. 23, 2010, now Pat. No. 9,028,495.

(51) Int. Cl.
*A61B 18/14*    (2006.01)
*A61B 17/29*    (2006.01)
(Continued)

(52) U.S. Cl.
CPC .......... *A61B 18/1445* (2013.01); *A61B 17/29* (2013.01); *A61B 17/295* (2013.01);
(Continued)

(58) Field of Classification Search
CPC ................. A61B 17/29; A61B 17/295; A61B 2017/0046; A61B 2017/00473; A61B 2017/294; A61B 18/1445
See application file for complete search history.

(56) References Cited

U.S. PATENT DOCUMENTS

D249,549 S    9/1978  Pike
D263,020 S    2/1982  Rau, III
(Continued)

FOREIGN PATENT DOCUMENTS

DE    2415263 A1    10/1975
DE    02514501 A1   10/1976
(Continued)

OTHER PUBLICATIONS

Office Action for European Application No. 11 170 965.5 dated Feb. 28, 2017.
(Continued)

*Primary Examiner* — Michael F Peffley
*Assistant Examiner* — Samantha M Good (57) ABSTRACT

A surgical instrument includes an elongated shaft having a proximal structural member and a proximal drive member that is selectively movable with respect to the proximal structural member. A modular end effector is removably coupled to the elongated shaft, and has a distal structural member and a distal drive member that is operatively coupled to a pair of jaw members. A separable joint is defined between the elongated shaft and the end effector. The separable joint includes laterally prominent and laterally indented portions of each of the proximal and distal structural members and of each of the proximal and distal drive members. The structural members are interlocked to resist longitudinal separation and permit lateral separation. The drive members are movable relative to structural members to move the separable joint to a locked configuration wherein the drive members prohibit lateral separation of the structural members.

10 Claims, 5 Drawing Sheets

(51) Int. Cl.
*A61B 17/00* (2006.01)
*A61B 18/00* (2006.01)
*A61B 17/295* (2006.01)

(52) U.S. Cl.
CPC ............... *A61B 2017/0046* (2013.01); *A61B 2017/00473* (2013.01); *A61B 2017/294* (2013.01); *A61B 2018/0063* (2013.01); *A61B 2018/00178* (2013.01); *Y10T 29/49826* (2015.01)

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| 5,282,806 A | 2/1994 | Haber et al. |
| D348,930 S | 7/1994 | Olson |
| D349,341 S | 8/1994 | Lichtman et al. |
| 5,334,215 A | 8/1994 | Chen |
| D354,564 S | 1/1995 | Medema |
| D358,887 S | 5/1995 | Feinberg |
| 5,575,805 A | 11/1996 | Li |
| 5,582,617 A | 12/1996 | Klieman et al. |
| 5,611,798 A | 3/1997 | Eggers |
| D384,413 S | 9/1997 | Zlock et al. |
| 5,665,100 A | 9/1997 | Yoon |
| 5,792,165 A | 8/1998 | Klieman et al. |
| D402,028 S | 12/1998 | Grimm et al. |
| 5,951,549 A | 9/1999 | Richardson et al. |
| D416,089 S | 11/1999 | Barton et al. |
| 6,053,933 A | 4/2000 | Balazs et al. |
| D424,694 S | 5/2000 | Tetzlaff et al. |
| D425,201 S | 5/2000 | Tetzlaff et al. |
| 6,270,508 B1 | 8/2001 | Klieman et al. |
| 6,277,117 B1 | 8/2001 | Tetzlaff et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| 6,409,728 B1 | 6/2002 | Ehr et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,255,697 B2 | 8/2007 | Dycus et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 8,070,748 B2 | 12/2011 | Hixson et al. |
| 8,092,451 B2 | 1/2012 | Schechter et al. |
| 8,112,871 B2 | 2/2012 | Brandt et al. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| 8,215,182 B2 | 7/2012 | Artale et al. |
| 8,257,352 B2 | 9/2012 | Lawes et al. |
| 8,266,783 B2 | 9/2012 | Brandt et al. |
| 8,287,536 B2 | 10/2012 | Mueller et al. |
| 8,292,886 B2 | 10/2012 | Kerr et al. |
| 8,298,233 B2 | 10/2012 | Mueller |
| 8,323,310 B2 | 12/2012 | Kingsley |
| 8,343,150 B2 | 1/2013 | Artale |
| 8,343,151 B2 | 1/2013 | Siebrecht et al. |
| 8,348,948 B2 | 1/2013 | Bahney |
| 8,357,159 B2 | 1/2013 | Romero |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Homer et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Homer |
| 8,491,626 B2 | 7/2013 | Roy et al. |
| 8,512,336 B2 | 8/2013 | Couture |
| 8,512,371 B2 | 8/2013 | Kerr et al. |
| 8,540,749 B2 | 9/2013 | Garrison et al. |
| 8,556,929 B2 | 10/2013 | Harper et al. |
| 8,568,397 B2 | 10/2013 | Homer et al. |
| 8,568,412 B2 | 10/2013 | Brandt et al. |
| 8,585,736 B2 | 11/2013 | Homer et al. |
| 8,597,295 B2 | 12/2013 | Kerr |
| 8,623,018 B2 | 1/2014 | Homer et al. |
| 8,641,712 B2 | 2/2014 | Couture |
| 8,641,713 B2 | 2/2014 | Johnson et al. |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,115 B2 | 3/2014 | Reschke |
| 8,734,445 B2 | 5/2014 | Johnson et al. |
| 8,740,898 B2 | 6/2014 | Chojin et al. |
| 2005/0131396 A1* | 6/2005 | Stanczak ........ A61B 17/320016 606/1 |
| 2008/0021278 A1 | 1/2008 | Leonard et al. |
| 2009/0206131 A1* | 8/2009 | Weisenburgh, II .......................... A61B 17/07207 227/175.2 |
| 2010/0274244 A1 | 10/2010 | Heard |
| 2010/0280511 A1 | 11/2010 | Rachlin et al. |
| 2010/0307934 A1 | 12/2010 | Chowaniec et al. |
| 2010/0331839 A1 | 12/2010 | Schechter et al. |
| 2011/0034918 A1 | 2/2011 | Reschke |
| 2011/0054468 A1 | 3/2011 | Dycus |
| 2011/0054471 A1 | 3/2011 | Gerhardt et al. |
| 2011/0060335 A1 | 3/2011 | Harper et al. |
| 2011/0071523 A1 | 3/2011 | Dickhans |
| 2011/0073594 A1 | 3/2011 | Bonn |
| 2011/0077648 A1 | 3/2011 | Lee et al. |
| 2011/0118736 A1 | 5/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0251605 A1 | 10/2011 | Hoarau et al. |
| 2011/0270245 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295313 A1 | 12/2011 | Kerr |
| 2011/0319888 A1 | 12/2011 | Mueller et al. |
| 2012/0022532 A1 | 1/2012 | Garrison |
| 2012/0041438 A1 | 2/2012 | Nau, Jr. et al. |
| 2012/0046662 A1 | 2/2012 | Gilbert |
| 2012/0059372 A1 | 3/2012 | Johnson |

(56) References Cited

U.S. PATENT DOCUMENTS

| | | |
|---|---|---|
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |

FOREIGN PATENT DOCUMENTS

| | | |
|---|---|---|
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 10200402617 | 12/2005 |
| DE | 20200700931 | 10/2007 |
| DE | 19738457 B4 | 1/2009 |
| EP | 1 159 926 A2 | 12/2001 |
| JP | 61-501068 | 9/1984 |
| JP | 10-24051 A | 1/1989 |
| JP | 65-502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09010223 A | 1/1997 |
| JP | 11-070124 A | 3/1999 |
| JP | 11-169381 A | 6/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |
| WO | 0036986 A1 | 6/2000 |
| WO | 0154604 A1 | 8/2001 |
| WO | 2005/110264 A2 | 11/2005 |

OTHER PUBLICATIONS

Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Int'l Search Report EP 07 015191.5 dated Jan. 23, 2008.
Int'l Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report PCT/US08/61498 dated Sep. 22, 2008.
Int'l Search Report PCT/US09/032690 dated Jun. 16, 2009.
U.S. Appl. No. 09/387,883, filed Sep. 1, 1999; inventor: Dale F. Schmaltz.
U.S. Appl. No. 09/591,328; filed Jun. 9, 2000; inventor: Thomas P. Ryan.
U.S. Appl. No. 12/336,970; filed Dec. 17, 2008; inventor: Paul R. Sremcich.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequen- (56) References Cited

OTHER PUBLICATIONS cies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Webpage—Cardica.com, "C-Port X-Change" Distal Anastomosis Systems, 2010 Cardica, Inc.
Webpage—Cardica.com, "XChange Reloading Video", 2010 Cardica, Inc.
In'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.

(56) References Cited

OTHER PUBLICATIONS

Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.

* cited by examiner

SURGICAL INSTRUMENT WITH A SEPARABLE COAXIAL JOINT

CROSS-REFERENCE TO RELATED APPLICATIONS

This application is a Divisional of U.S. patent application Publication Ser. No. 12/822,024, now U.S. Pat. No. 9,028,485, filed on Jun. 23, 2010, the entire contents of which hereby incorporated by reference.

BACKGROUND

1. Technical Field Separable

The present disclosure relates generally the field of reposable or reusable surgical instruments. In particular, the disclosure relates to instruments having separable and replaceable components to provide clean, sterile or refurbished surfaces in each instance of use.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws. A detailed discussion of the use of an electrosurgical forceps may be found in U.S. Pat. No. 7,255,697 to Dycus et al.

In use, various tissue-contacting components of an electrosurgical forceps tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use. In order to provide clean electrodes and a sharp knife for a particular surgical procedure, a brand new instrument is often used. Once the procedure is complete, the used instrument is discarded.

Instruments that may be reused for multiple procedures reduce the instrumentation costs per procedure. Some reusable forceps include a reusable base component adapted for persistent use and a removable and replaceable modular component adapted for limited use coupled thereto. The reusable base component may include, for example, a control element such as a handle that remains primarily outside the surgical field. The handle may be constructed ruggedly to sustain regular and recurring usage in numerous surgical procedures. The removable and replaceable component may include a tool element, such as an end effector containing delicate and tissue-contacting wear surfaces. Replacing a worn end effector to refurbish an instrument provides refreshed surfaces with minimal waste.

Providing replaceable components for a reusable electrosurgical forceps, however, presents various challenges. For example, many of these instruments require arduous disassembly and reassembly procedures to ensure proper mechanical and electrical connections are made between the reusable and replaceable components.

SUMMARY

The present disclosure describes a reusable surgical instrument for treating tissue. The instrument includes a handle assembly supporting a first actuator. An elongated shaft extends distally from the handle assembly and defines a longitudinal axis. The elongated shaft includes a proximal structural member and a proximal drive member, and the proximal drive member is operatively coupled to the first actuator such that manipulation of the first actuator induces movement of the proximal drive member relative to the proximal structural member. A modular end effector is removably coupled to the elongated shaft, and includes a distal structural member and a distal drive member. The distal drive member is operatively coupled to a pair of jaw members such that movement of the distal drive member relative to the distal structural member induces movement of the jaw members between an open configuration wherein the jaw members are substantially spaced to a closed configuration wherein the jaw members are closer together. A separable joint is defined between the elongated shaft and the end effector. The separable joint includes a laterally prominent portion and a laterally indented portion defined on each of the proximal and distal structural members and configured to interlock with one another such that the proximal and distal structural members resist longitudinal separation and permit separation in a lateral direction. Laterally prominent portions and a laterally indented portions defined on the proximal and distal drive members are configured to interlock with one another such that the proximal and distal drive members transmit motion therebetween and permit separation in the at least one lateral direction. The drive members are movable relative to the structural members to move the separable joint between a locked configuration wherein the drive members prohibit separation of the structural members and an unlocked configuration wherein the drive members permit separation of the structural members in the lateral direction.

The structural members may define a generally tubular configuration about the longitudinal axis, and the drive members may be coaxially-arranged with respect to the structural members. The first actuator may be operable to induce longitudinal motion in the drive members to move the jaw members between the first and second configurations. The handle assembly may also support a second actuator, and the second actuator may be operable to induce rotational motion of the drive members to rotate the jaw members about the longitudinal axis.

The end effector may include a knife selectively movable through the jaw members, and the separable joint may include separable and interlocking portions of a distal knife rod and a proximal knife rod. The distal knife rod may be operatively coupled to the knife to move the knife through the jaw members, and the proximal knife rod selectively movable with respect to the structural members from the handle assembly.

The end effector may include an electrode configured for delivering electrosurgical energy to tissue, and the separable joint may include first and second electrical connectors. The first electrical connector may be supported by the elongated shaft and may be electrically coupled to a source of electrosurgical energy. The second electrical connector may be supported by the end effector and electrically coupled to the at least one electrode. The first and second electrical connectors may be configured to engage and disengage one another in the lateral direction in which the structural members are separable.

The interlocking portions of the structural members may define a first outer diameter. The distal structural member may be coupled to the end effector by a shaft portion defining a second outer diameter that is smaller than the first outer diameter.

According to another aspect of the disclosure, a method of assembling a surgical instrument includes the steps of providing the instrument with the end effector separated from the elongated shaft. Next, the elongated shaft and the end effector may be approximated in a lateral direction to simultaneously engage the proximal structural member with the distal structural member, and the proximal drive member with the distal drive member. Finally, the first actuator may be manipulated to move the drive members into a longitudinal position wherein the drive members prohibit separation of the structural members in the lateral direction.

According to another aspect of the disclosure, a surgical instrument includes a handle assembly supporting an actuator. A proximal tubular member extends distally from the handle assembly and defines a longitudinal axis. The proximal tubular member includes an inter-engaging mating portion at a distal end thereof. A proximal drive member extends through the proximal tubular member and is operatively coupled to the actuator such that manipulation of the actuator induces longitudinal movement of the proximal drive member relative to the proximal tubular member. The proximal drive member includes an inter-engaging mating portion at a distal end thereof. An end effector includes a movable end effector element adapted for moving between first and second configurations for manipulating tissue. A distal tubular member extends proximally from the end effector, and includes an inter-engaging mating portion at a proximal end thereof corresponding to the inter-engaging mating portion of the proximal tubular member. A distal drive member extends through the distal tubular member. The distal drive member is operatively coupled to the movable end effector element such that longitudinal movement of the distal drive member induces the movable end effector element to move between the first and second configurations. The distal drive member includes an inter-engaging mating portion at a proximal end thereof corresponding to the inter-engaging mating portion of the proximal drive member. The proximal drive member is movable from an unlocked configuration wherein the inter-engaging mating portion of the proximal drive member is generally aligned with the inter-engaging mating portion of the proximal tubular member to permit lateral engagement and disengagement of the inter-engaging mating portions of the tubular members and drive members simultaneously, and a locked configuration wherein the inter-engaging mating portion of the proximal drive member is longitudinally displaced with respect to the inter-engaging mating portion of the proximal tubular member. In the locked configuration, the proximal drive member is within one of the proximal and distal tubular members such that lateral disengagement of the inter-engaging mating portions of the tubular members and drive members is prohibited.

The movable end effector element may include a pair of jaw members movable between an open configuration wherein the jaw members are substantially spaced to a closed configuration wherein the jaw members are closer together. Each of the inter-engaging mating portions of the tubular members may include a laterally prominent hook portion and a laterally indented portion for receiving the hook portion of the inter-engaging mating portion of the other tubular member.

The actuator may be operable to move the proximal drive member between the locked and unlocked configurations, and to move the movable end effector element between the first and second configurations. The end effector may include an electrode disposed thereon adapted for delivering electrosurgical energy to tissue.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
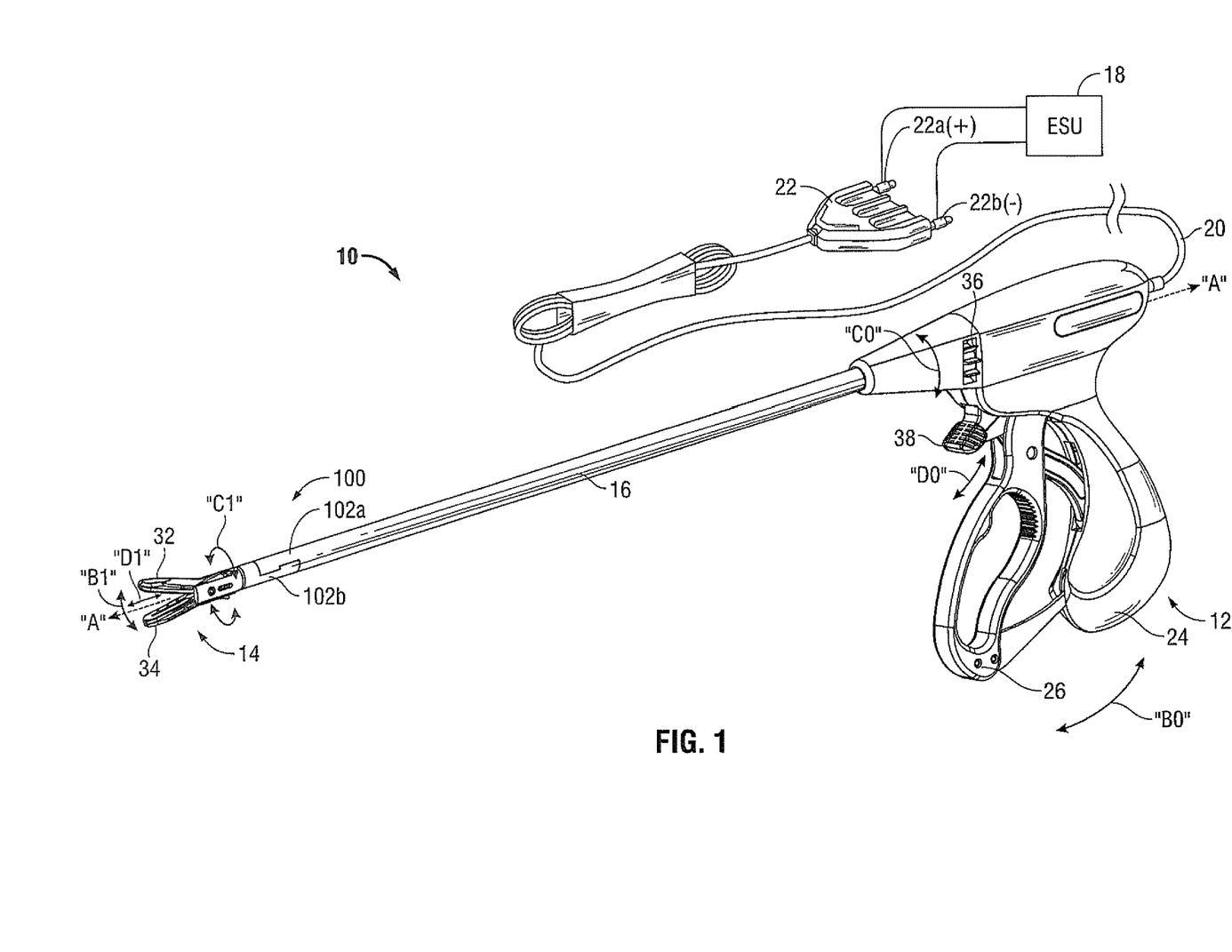
FIG. 1 is a perspective view of an endoscopic surgical instrument in accordance with the present disclosure having a modular end effector removably coupled to a distal end of an elongated shaft by a separable coaxial joint.

Referring initially to FIG. 1, an embodiment of an electrosurgical instrument 10 is depicted. The instrument 10 includes a handle assembly 12, a modular end effector 14 and an elongated shaft 16 therebetween defining a longitudinal axis A-A. A surgeon may manipulate the handle assembly 12 to remotely control the end effector 14 through the elongated shaft 16. This configuration is typically associated with instruments for use in laparoscopic or endoscopic surgical procedures. Various aspects of the present disclosure may also be practiced with traditional open instruments and in connection with endoluminal procedures as well.

The instrument 10 is coupled to a source of electrosurgical energy, e.g., an electrosurgical generator 18. The generator 18 may include devices such as the LIGASURE® Vessel Sealing Generator and the Force Triad® Generator as sold by Covidien. A cable 20 extends between the handle assembly 12 and the generator 18, and includes a connector 22 for coupling the instrument 10 to the generator 18. The connector 22 includes two prong members 22a and 22b that are dimensioned to mechanically and electrically connect the instrument 10 to opposite poles (+), (−) associated with the generator 18. Thus, bipolar energy may be provided through the instrument 10. Alternatively, the instrument 10 may be configured for delivering monopolar energy to the tissue. In a monopolar configuration, the instrument 10 delivers electrosurgical energy of a first potential, e.g. (+), while a return pad (not shown) is placed generally beneath a patient and provides a return path to the opposite pole, e.g. (−), of the generator 18. A footswitch (not shown) may be provided to initiate and terminate the delivery of electrosurgical energy to the end effector 14.

To control movement of the end effector 14, the handle assembly 12 includes various actuators that may be manipulated by a surgeon during a surgical procedure. The actuators include a stationary handle 24 and movable handle 26 that may be separated and approximated relative to one another, in the direction of arrows "B0," to respectively open and close a pair of jaw members 32, 34 in the direction of arrows "B1." A surgeon may also rotate a rotation knob 36 about the longitudinal axis A-A in the direction of arrows "C0" to rotate the end effector 14 about the longitudinal axis A-A in the direction of arrows "C1." The embodiment depicted in FIG. 1 may be considered a "tip rotation" embodiment since manipulation of the rotation knob 36 induces rotation only at the distal "tip" of the elongated shaft 16, e.g., only the end effector 14. As described in greater detail below, the rotation knob 36 is coupled to interior components of the elongated shaft 16 to cause the end effector 14 to rotate. The outermost components of the elongated shaft 16 remain stationary relative to the stationary handle 24. Other embodiments are contemplated in which the outermost components of the elongated shaft 16 may be induced to rotate. These embodiments may be considered "shaft rotation" embodiments. A more detailed discussion of a "shaft rotation" instrument may be found in the above mentioned U.S. Pat. No. 7,255,697 to Dycus et al.

Another actuator provided on the handle 12 is trigger 38. Trigger 38 is movable relative to the stationary handle 24 in the direction of arrows "D0," and is operable to extend and retract a knife 40 (FIG. 3) through the end effector 14 in the direction of arrows "D1." Each of theses actuators is mechanically coupled to the end effector 14 through the elongated shaft 16 as described in greater detail below.

A separable coaxial joint 100 is defined between the end effector 14 and the elongated shaft 16. The joint 100 permits the end effector 14 to be removed from the elongated shaft 16 such that a new or refurbished end effector (not shown) may be coupled to the elongated shaft 16 following a surgical procedure. The handle assembly 12 may be subsequently reused with the new or refurbished end effector. As described in greater detail below, the joint 100 includes a first mating component 102a defined at a distal end of the elongated shaft 16 and a second mating component 102b defined at a proximal end of the end effector 14. The first and second mating components 102a and 102b provide electrical connections to operatively couple the end effector 14 to the generator 18 and the mechanical connections to operatively couple the end effector 14 to the actuators, e.g., movable handle 26, rotation knob 36 and trigger 38. The joint 100 provides a positive mechanical connection between the end effector 14 and the elongated shaft 16 such that the end effector 14 will not inadvertently be detached during a surgical procedure.

Figure 2:
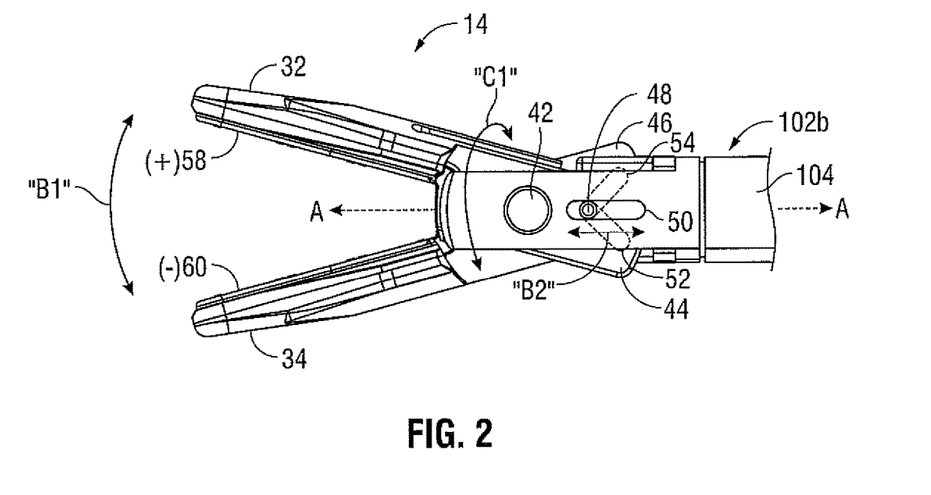
FIG. 2 is an enlarged, side view of the end effector of FIG. 1 depicting a pair of jaw members in an open configuration.

Referring now to FIG. 2, end effector 14 is depicted in an open configuration wherein upper and lower jaw members, 32 and 34 respectively, are substantially spaced from one another. In the open configuration, the jaw members 32, 34 may be maneuvered into position to capture tissue therebetween. To facilitate maneuvering the end effector 14 into position, the end effector 14 may be rotated about longitudinal axis A-A with respect to an outer tubular member 104 of the second mating component 102b. The outer tubular member 104 thus provides a distal stationary reference structure for various relative motions of the end effector 14. The end effector 14 is operatively coupled to the rotation knob 36 (FIG. 1) through the through separable coaxial joint 100 as described below with reference to FIGS. 4 through 7B.

Each of the jaw members 32, 34 is coupled to the second mating portion 102b about a pivot pin 42 such that the jaw members 32, 34 are pivotable to a closed configuration (FIG. 3) where the jaw members 32, 34 are closer together to clamp the tissue therebetween. The jaw members 32, 34 include respective proximal drive flanges 44, 46 extending into the second mating portion 102b, where the proximal drive flanges 44, 46 engage a drive pin 48. The drive pin 48 is movably disposed in a longitudinal drive slot 50 extending through the second mating portion 102b. The drive pin is operatively associated with the movable handle 26 (FIG. 1) through the separable coaxial joint 100 to reciprocate through the drive slot 50. Each of the proximal drive flanges 44, 46 of the jaw members 32, 34 include a respective cam slot 52, 54 that engages the drive pin 48 as the drive pin 48 reciprocates through the longitudinal drive slot 50. The cam slots 52 and 54 are disposed obliquely with respect to the longitudinal drive slot 50 such that longitudinal movement of the drive pin 48 in the direction of arrows "B2" induce the jaw members 32, 34 to pivot about the pivot pin 42 in the direction of arrows "B1." This type of construction induces bilateral jaw motion. Other unilateral constructions are also envisioned in which only one of the jaw members 32, 34 moves with respect to the elongated shaft 16 to move between the open and closed configurations.

The pair of jaw members 32, 34 includes a pair of opposed electrodes 58, 60 positioned to contact tissue situated between the jaw members 32, 34. The opposed electrodes 58, 60 are associated with opposite electrical potentials (+), (−) to permit an electrosurgical current to flow through the tissue situated between the jaw members 32, 34. The electrosurgical current, when applied in conjunction with an appropriate amount of pressure to the tissue, may effect a tissue seal. To form an effective tissue seal, a relatively high clamping force is typically generated to impart a closure pressure on the tissue in the range of from about 3 kg/cm$^2$ to about 16 kg/cm$^2$. An appropriate gap distance of about 0.001 inches to about 0.006 inches may be maintained between the electrodes 58 and 60, although other gap distances are contemplated.

Figure 3:
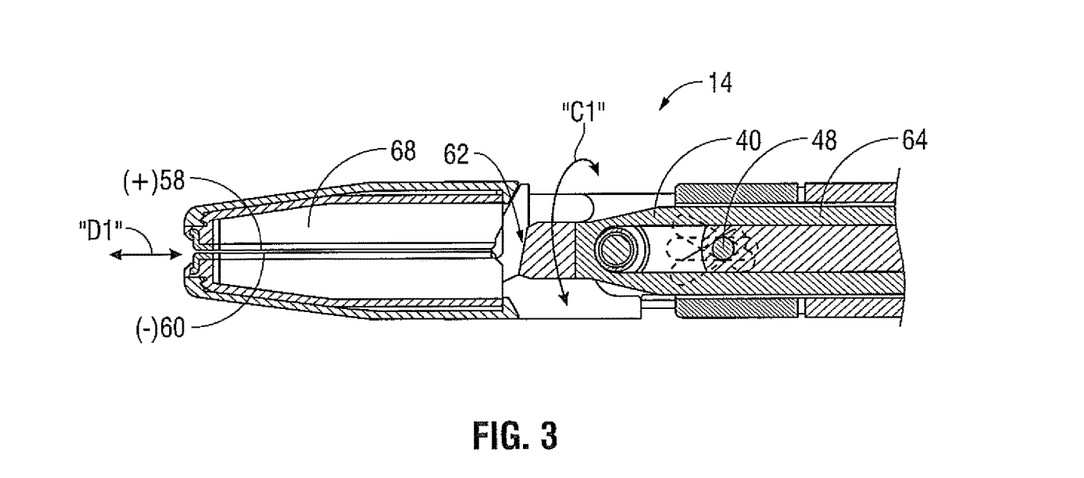
FIG. 3 is an enlarged, cross-sectional view of the end effector depicting the jaw members in a closed configuration, and a reciprocating knife in a retracted position.

Referring now to FIG. 3, end effector 14 is depicted in a closed configuration wherein the upper and lower jaw members 32, 34 are closer together than when in the open configuration. The drive pin 48 is moved to a proximal position in the drive slot 50 and cam slots 52, 54 to induce the jaw members 32, 34 to pivot toward one another about pivot pin 42. In the closed configuration, the jaw members 32, 34 may apply a clamping force to tissue, and the electrodes may deliver electrosurgical energy to the tissue to generate a tissue seal. Thereafter, the reciprocating knife 40 may be advanced to transect the sealed tissue captured between the jaw members 32, 34.

The reciprocating knife 40 includes a sharp distal edge 62 and a bifurcated proximal shank 64. The proximal shank 64 is operatively coupled to the trigger 38 (FIG. 1) through separable coaxial joint 100 as described below with reference to FIGS. 4 through 7. The trigger 38 is operable to drive the knife 40 in a longitudinal direction "D1." The sharp distal edge 62 may be driven into a knife channel 68 defined in each of the jaw members 32, 34, and thus, sealed tissue captured between the electrodes 58, 60 may be transected. The knife 40 may be rotated about longitudinal axis A-A in the direction of arrows "C1" along with the end effector 14, and thus, the knife 40 may be operable irrespective of the rotational orientation of the end effector 14.

Figure 4:
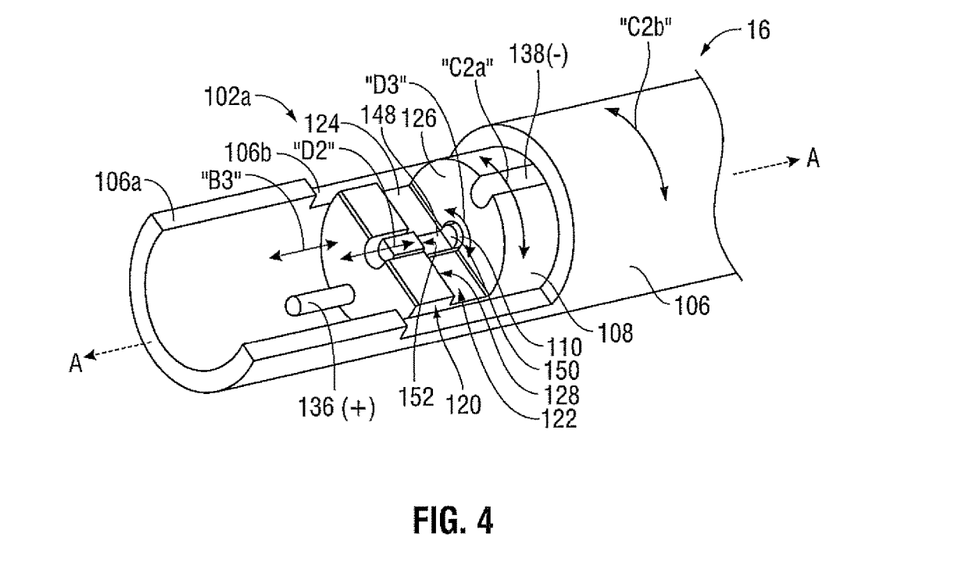
FIG. 4 is a perspective view of an underside of the distal end of the elongated shaft defining a first mating component of the separable coaxial joint.
Figure 5:
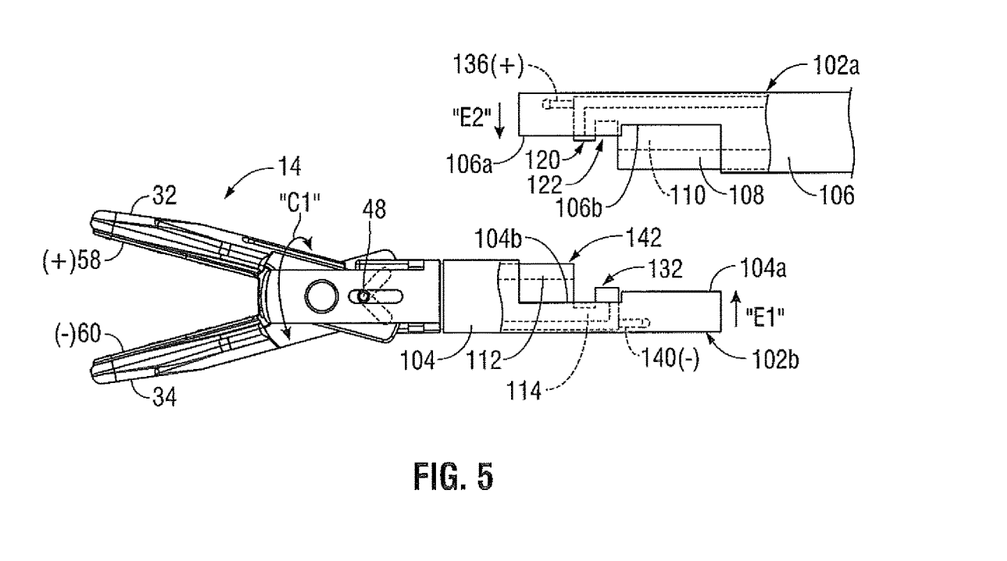
FIG. 5 is a side view of the modular end effector defining a second mating component separated from the first mating component of the separable coaxial joint in a lateral direction.

Referring now to FIGS. 4 and 5, a distal end of elongated shaft 16 defines first mating component 102a. The first mating component 102a includes a structural, outer tubular member 106, a radially intermediate, proximal jaw drive shaft 108, and a central, proximal knife drive rod 110. The outer tubular member 106 may be fixedly coupled to stationary handle 24 (FIG. 1) and thus provides a proximal stationary reference structure for the relative motions of the proximal jaw drive shaft 108 and the proximal knife drive rod 110. Alternatively, in a "shaft rotation" embodiment (not shown) the outer tubular member 106 may be fixedly coupled to an actuator configured to rotate relative to the stationary handle 24.

The proximal jaw drive shaft 108 is operatively coupled to the movable handle 26 (FIG. 1) such that manipulation of the movable handle 26 induces longitudinal motion of the proximal jaw drive shaft 108 relative to the outer tubular member 106 in the direction of arrows "B3." The proximal jaw drive shaft 108 is also operatively coupled to the rotation knob 36 such that manipulation of the rotation knob 36 induces rotational motion of the proximal jaw drive shaft 108 relative to the stationary outer tubular member 106 in the direction of arrows "C2a." In an alternative "shaft rotation" embodiment (not shown) the outer tubular member 106 may be induced to rotate in the direction of arrows "C2b." The proximal knife drive rod 110 is operatively coupled to the trigger 38 (FIG. 1) such that manipulation of the trigger 38 induces longitudinal motion of the proximal knife drive rod 110 in the direction of mows "D2." The proximal knife drive rod 110 is longitudinally movable with respect to the proximal jaw drive shaft 108, but may maintain a rotational orientation with respect to the proximal jaw drive shaft 108. The proximal knife drive rod 110 may be keyed to the jaw drive shaft 108 such that rotational motion of the proximal jaw drive shaft 108 in the direction of arrows "C2a" induces a corresponding rotational motion of the proximal knife drive rod 110 in the direction of arrows "D3." In other embodiments, the proximal jaw drive shaft 108 and proximal knife drive rod 110 may be independently rotatable with respect to one another.

Each of the outer tubular member 106, proximal jaw drive shaft 108 and proximal knife drive rod 110 exhibits an undercut profile at the distal end thereof. This profile permits each component 106, 108, 110 of the first mating component 102a to interlock with respective corresponding component of the second mating component 102b (see FIG. 5). For example, the outer tubular member 106 of the first mating component 102a interlocks with the outer tubular member 104 of the second mating component 102b. The outer tubular member 106 exhibits an undercut profile as exemplified by a laterally prominent distal hook portion 106a and a laterally indented, recessed or undercut hook receiving portion 106b. A laterally prominent hook portion 104a of the outer tubular member 104 may be received in the hook receiving portion 106b, and a hook receiving portion 104b of the outer tubular member 104 may receive the hook portion 106a of outer tubular member 106. When thus engaged, the outer tubular members 104, 106 are axially aligned about the longitudinal axis A-A, and resist longitudinal separation because of the interlocking hook portions 104a, 106a. However, the outer tubular members 104, 106 are susceptible to lateral separation as described in greater detail below.

Inner drive members 108, 110, 112, 114 of first and second mating components 102a and 102b also exhibit interlocking undercut profiles. For example, the proximal jaw drive shaft 108 interlocks with a distal jaw drive shaft 112 and the proximal knife drive rod 110 interlocks with a distal knife drive rod 114. This interlocking arrangement permits the motions the proximal jaw drive shaft 108 and proximal knife drive rod 110 of the first mating component 102a to be transmitted the distal jaw drive shaft 112 and distal knife drive rod 114 of the second mating component 102b. Additional inner members (not shown) may be provided in other embodiments to provide additional functionality to the end effector 14 by enabling additional independent movements to be transmitted between the handle assembly 12 and the end effector 14.

The undercut profile of the inner drive members 108, 110, 112, 114 is exemplified by the proximal jaw drive shaft 108 as depicted in FIG. 4. The interlocking portion of the proximal jaw drive shaft 108 includes a laterally prominent, distal hook portion 120 and a laterally indented, proximal hook receiving portion 122. The hook receiving portion 122 is undercut with respect to the hook portion 120 in that the hook receiving portion 122 is less prominent laterally than the hook portion 120. The hook receiving portion 122 includes a floor surface 124 that lies in a plane parallel to the longitudinal axis A-A, and pair of wall surfaces 126 and 128 that lie in planes perpendicular to the longitudinal axis A-A.

Figure 6:
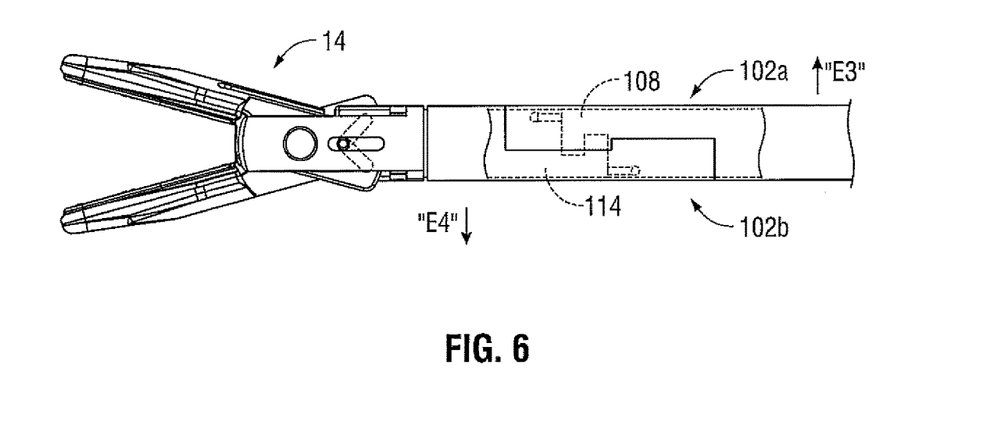
FIG. 6 is a side view of the first and second mating components of the separable coaxial joint adjacent one another in an unlocked configuration wherein the first and second mating components may be separated in the lateral direction.

The floor surface 124 is arranged to transfer torque to the distal jaw drive shaft 112 as the proximal jaw drive shaft 108 is rotated in the direction of arrows "C2a." The wall surfaces 126 and 128 are arranged to transfer compressive and tensile loads respectively to the distal jaw drive shaft 112 as the proximal jaw drive shaft 108 is translated in the direction of arrows "B3." A hook portion 132 of the second jaw drive shaft is configured to engage the floor surface 124 and wall surfaces 126, 128 of the proximal jaw drive shaft 108 when the proximal and distal jaw drive shafts 108, 112 are interlocked (see FIG. 6). The hook portion 132 may thus receive the longitudinal and rotational mechanical forces for driving the jaw members 32, 34. Specifically, the compressive and tensile loads may be transmitted to the drive pin 48 to open and close the jaw members 32, 34, and the torsional loads may be transmitted to the end effector 14 to rotate the end effector 14 in the direction of arrows "C1" as described above with reference to FIGS. 2 and 3.

Electrical connectivity may also be established by interlocking the first and second jaw drive shafts 108, 112. The proximal jaw drive shaft 108 includes an electrically conductive pin 136 protruding from a distal end thereof and an electrically conductive pin-receiving slot 138 on a lateral side thereof. The pin 136 and slot 138 may be electrically coupled to opposite poles (+), (−) of the generator 18 (FIG. 1). The slot 138(−) is configured to receive an electrically conductive pin 140(−) protruding from a proximal end of the distal jaw drive shaft 112. The electrically conductive pin 140(−) is in electrical communication with electrode 60(−). Thus, by establishing electrical communication between the slot 138 and the pin 140, electrical connectivity may be established between the electrode 60 and the generator 18. Similarly, the pin 136 may be electrically coupled to a slot 142 defined in the distal jaw drive shaft 112 to establish electrical continuity between electrode 58(+) and the generator 18.

The proximal knife drive rod 110 also exhibits an undercut profile that allows the proximal knife drive rod 110 to transmit torsional, compressive and tensile loads to the distal knife drive rod 114 of the second mating component 102b. The proximal knife drive rod 110 includes a floor surface 148 for transmitting torsional loads and wall surfaces 150, 152 for transmitting compressive and tensile loads. The proximal knife drive rod 110 is operatively coupled to the trigger 38 (FIG. 1) and the distal knife drive rod 114 is operatively coupled to the knife 64. Thus, interlocking first and second knife drive rods 110, 114 operatively couples the knife 64 with the trigger 38.

Referring now to FIGS. 5 through 7B, a procedure for interlocking the first and second mating components 102a, 102b is described. First, the proximal jaw drive shaft 108 and proximal knife drive rod 110 are moved longitudinally to a mating location with respect to the outer tubular member 106 as depicted in FIG. 5. An appropriate longitudinal mating location is where the inter-engaging mating portion of the proximal jaw drive shaft 108 is generally aligned with the inter-engaging mating portion of the proximal tubular member 106 such that the laterally prominent hook portion 120 and laterally indented hook receiving slot 122 are exposed on an open lateral side of the tubular member 106. In this mating position, the laterally prominent portions of the proximal jaw drive shaft 108 and proximal knife drive rod 110 are aligned with the laterally indented portions of the distal jaw drive shaft 112 and distal knife drive rod 114 respectively, and the laterally prominent portions 160a of the outer tubular member 106 are aligned with the laterally indented portions 104b of the outer tubular member 104.

The movable handle 26 and the trigger 38 (FIG. 1) may be employed to move the proximal jaw drive shaft 108 and first knife drive shaft may be moved to the mating position. Various mechanisms such as detents or other indicators may be incorporated into the actuators 26, 38 to provide a tactile indication that the mating location has been achieved. The mating location may be achieved by moving the actuators to a location outside the range of motion required for normal use of the instrument 10. Similarly, a rotational orientation of the proximal jaw drive shaft 108 and proximal knife drive rod 110 may be achieved using rotation knob 36. The mating rotational orientation is characterized in that the pins 136, 140 align with the respective slots 142, 138.

When an appropriate mating location and orientation is achieved, the first and second mating portions 102a, 102b may be approximated in a lateral direction indicated by arrows "E1" and "E2" in FIG. 5 to the engaged configuration of FIG. 6. With this single lateral motion, simultaneously the outer tubular member 106 interlocks with the outer tubular member 104, the proximal jaw drive shaft 108 interlocks with the distal jaw drive shaft 112, the proximal knife drive rod 110 interlocks with the distal knife drive rod 114, and the pins 136, 140 engage the respective slots 142, 138. The configuration of FIG. 6, however, may be characterized as an unlocked configuration. This is because the first and second mating portions 102a, 102b may be laterally separated by applying laterally directed forces to the first and second mating portions 102a, 102b in the relative directions of arrows "E3" and "E4."

Figure 7A:
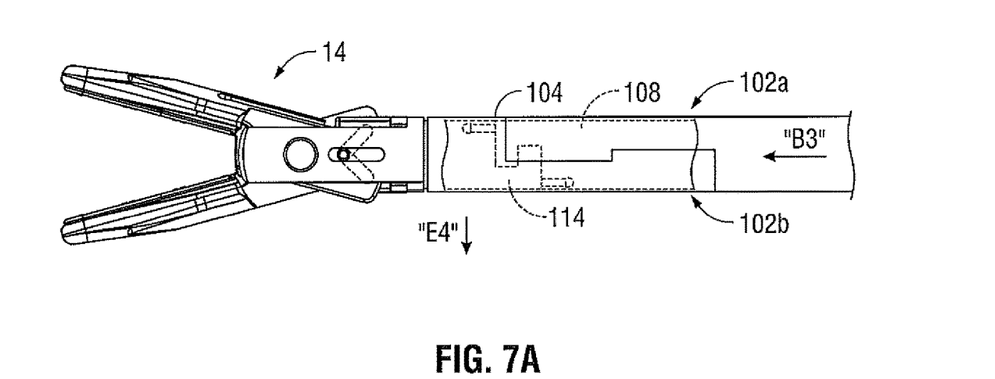
FIG. 7A is a side view of the first and second mating components of the separable coaxial joint adjacent one another in a locked configuration wherein the first and second mating components resist separation in the lateral direction.

The first and second mating components 102a, 102b may be moved to a locked configuration as depicted in FIG. 7A, wherein the first and second mating components 102a, 102b resist separation from one another. The proximal jaw drive shaft 108 may be advanced distally until a portion of the proximal jaw drive shaft 108 extends into outer tubular member 104 of the second mating component 102b. This arrangement causes interference between the proximal jaw drive shaft 108 and the outer tubular member 104, prohibiting the separation of the first and second mating components 102a, 102b in the lateral direction of arrows "E3" and "E4." The movable handle 26 (FIG. 1) may again be employed to advance the proximal jaw drive shaft 108 to the locked position of FIG. 7A. Alternatively, the proximal jaw drive shaft 108 may be retracted proximally until the proximal jaw drive shaft 108 and a portion of the second jaw drive shaft 114 is drawn into the first mating component 102a to lock the first and second mating components 102a, 102b.

Figure 7B:
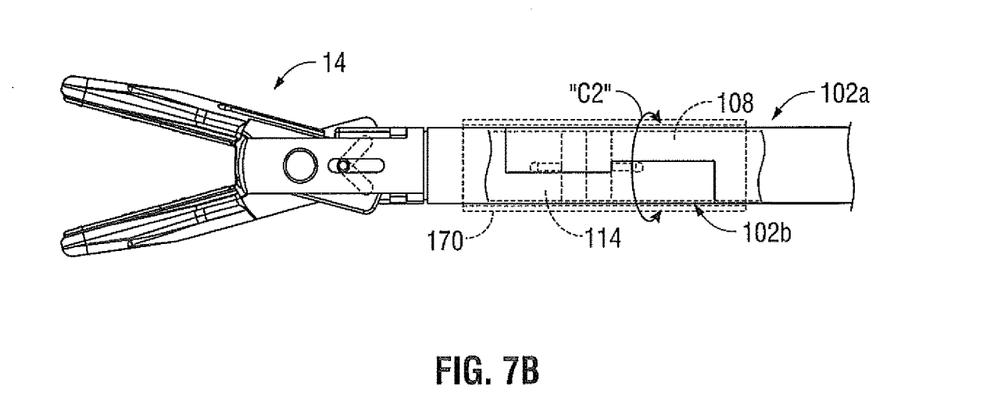
FIG. 7B is a side view of the first and second mating components in an alternate locked configuration.

Similarly, the proximal jaw drive shaft 108 may be rotated in the direction of arrows "C2a" to move the first and second mating components 102a, 102b to the locked configuration depicted in FIG. 7B. In this locked configuration, the lateral direction in which the outer tubular members 104, 106 tend to separate is dissimilar from the lateral direction in which the first and second jaw drive shafts 108, 114 tend to separate. Thus, the first and second mating components 102a, 102b are positively locked since there is no lateral direction in which all interlocking members of the first and second mating components 102a, 102b will tend to separate. The rotation knob 36 may be employed to rotate the proximal jaw drive shaft 108 into the locked configuration of FIG. 7B.

Various other locked configurations are contemplated. For example, an additional tubular member 170 (shown in phantom in FIG. 7B) may be placed over the first and second mating components 102a, 102b to prohibit separation thereof. An inner diameter of the tubular member 170 is slightly larger than an outer diameter of the outer tubular members 104, 106. Also, a locked configuration may be achieved by translating the first knife rod 110 (FIG. 4). The trigger 38 may be employed to advance the first knife rod 110 into the second jaw drive shaft 114, and thus create an interference that prohibits separation of the first and second mating components 102a, 102b. Any combination of translation and rotation of the proximal jaw drive shaft 108 and the first knife rod 110 may be employed to move the first and second mating components 102a, 102b from the unlocked mating configuration of FIG. 6 to a locked configuration suitable for performing a surgical procedure. Following the procedure, the proximal jaw drive shaft 108 and the first knife rod 110 may be returned to the unlocked configuration of FIG. 6 to permit de-mating of the first and second mating components 102a, 102b.

Figure 8:
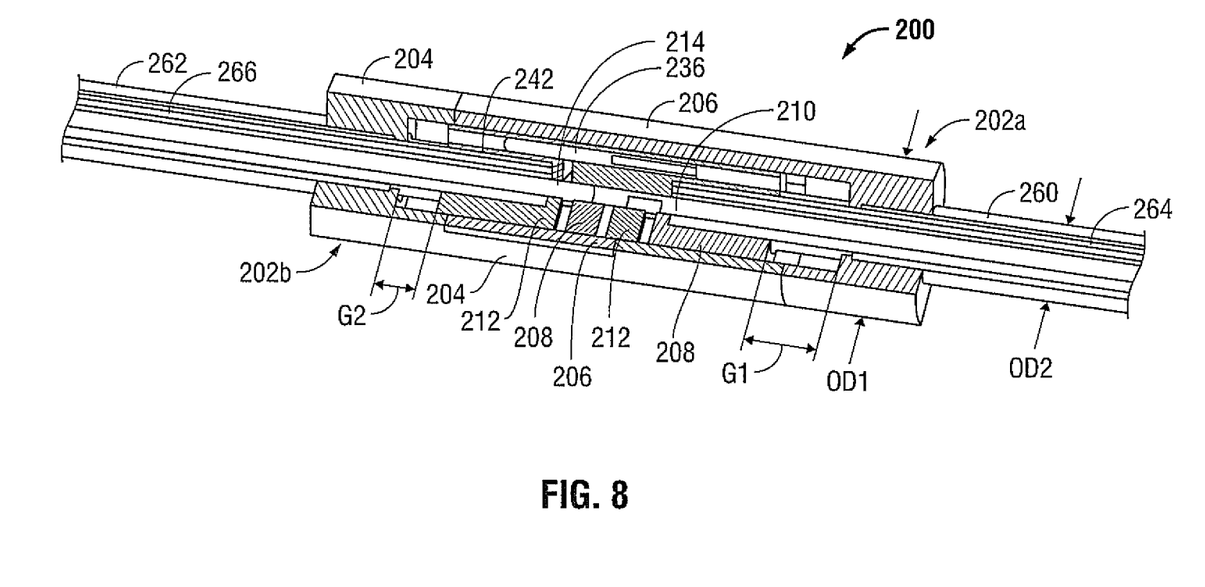
FIG. 8 is a sectional, perspective view of an alternate embodiment of a separable coaxial joint in a locked configuration.

Referring now to FIG. 8, another embodiment of a separable coaxial joint 200 is depicted with first and second mating components 202a, 202b in a locked configuration. The first and second mating components 202a, 202b include outer tubular members 204, 206 each exhibiting an undercut profile that permits the outer tubular members 204, 206 to interlock with one another and resist longitudinal separation. First and second jaw drive shafts 208, 212, and first and second knife rods 210, 214 interlock to transmit rotational and longitudinal motion, and a pin 236 engages slot 242 to transmit electrical energy between the first and second mating components 202a, 202b.

Outer tubular members 204, 206 exhibit a first outer diameter OD1 that is sufficiently large to facilitate manual manipulation of the separable coaxial joint 200 such that the first and second mating components 202a, 202b may be laterally approximated by hand. The first outer diameter OD1 also provides robustness to the outer tubular members 204, 206 that permits the coaxial joint 200 to withstand the various loads that may tend to separate first and second mating components 202a, 202b. In some applications, it may be advantageous for portions of an elongated shaft to exhibit an outer diameter OD2 that is smaller than the first outer diameter OD1. For example, the portions of an elongated shaft that enter a surgical field in an endoscopic procedure may be configured with a smaller outer diameter OD2 to permit the procedure to be performed through a smaller incision.

Outer tubular member 204 is fixedly coupled to a shaft portion 260 extending proximally therefrom. The shaft portion 206 exhibits the smaller outer diameter OD2 and may couple the outer tubular member 204 to a reusable handle assembly of a surgical instrument. The outer tubular member 204 is fixedly coupled to a shaft portion 262 extending distally therefrom. The shaft portion 262 exhibits the smaller outer diameter OD2 and may couple the outer tubular member 204 to a modular end effector. A first jaw drive tube 264 extends slidably through the shaft portion 260, and may couple the proximal jaw drive shaft 208 to an actuator. A second jaw drive tube 266 extends slidably through the shaft portion 262, and may couple the second jaw drive shaft 212 to a jaw member on the end effector. Thus, the jaw drive tube 264 may be translated and rotated to induce a corresponding translation and rotation of first and second jaw drive shafts 208, 212 and the second jaw drive tube 262. The outer tubular members 204, 206 provide sufficient clearance for the first and second jaw drive shafts 208, 212 to translate through a distance of G1 and G2. This distance is sufficient to provide functionality to an end effector such as opening and closing a pair of jaw members.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a handle assembly supporting an actuator thereon;
   a proximal tubular member extending distally from the handle assembly and defining a longitudinal axis, the proximal tubular member including an inter-engaging mating portion at a distal end thereof;
   a proximal drive member extending at least partially through the proximal tubular member, the proximal drive member operatively coupled to the actuator such that manipulation of the actuator induces longitudinal movement of the proximal drive member relative to the proximal tubular member, the proximal drive member including an inter-engaging mating portion at a distal end thereof;
   an end effector including at least one movable end effector element adapted for moving between first and second configurations for manipulating tissue;
   a distal tubular member extending proximally from the end effector, the distal tubular member including an inter-engaging mating portion at a proximal end thereof corresponding to the inter-engaging mating portion of the proximal tubular member;
   a distal drive member extending at least partially through the distal tubular member, the distal drive member operatively coupled to the at least one movable end effector element such that longitudinal movement of the distal drive member induces the at least one movable end effector element to move between the first and second configurations, the distal drive member including an inter-engaging mating portion at a proximal end thereof corresponding to the inter-engaging mating portion of the proximal drive member; and
   a knife, a distal knife rod, and a proximal knife rod, the distal knife rod operatively coupled to the knife to move the knife along the longitudinal axis, the distal knife rod and the proximal knife rod separable from each other and including interlocking portions;
   wherein the proximal drive member is movable from an unlocked configuration wherein the inter-engaging mating portion of the proximal drive member is generally aligned with the inter-engaging mating portion of the proximal tubular member to permit lateral engagement and disengagement of the inter-engaging mating portions of the tubular members and the drive members simultaneously, and a locked configuration wherein the inter-engaging mating portion of the proximal drive member is longitudinally offset with respect to the inter-engaging mating portion of the proximal tubular member and within one of the proximal and distal tubular members such that lateral disengagement of the inter-engaging mating portions of the tubular members and the drive members is prohibited.

2. The surgical instrument according to claim 1, wherein the at least one movable end effector element includes two jaw members movable between an open configuration wherein the jaw members are substantially spaced to a closed configuration wherein the jaw members are closer together.

3. The surgical instrument according to claim 1, wherein each of the inter-engaging mating portions of the proximal tubular member and the distal tubular member includes a laterally prominent hook portion and a laterally indented portion for receiving the hook portion of the inter-engaging mating portion of the other tubular member.

4. The surgical instrument according to claim 1, wherein the actuator is operable to move the proximal drive member between the locked and unlocked configurations and to move the at least one movable end effector element between the first and second configurations.

5. The surgical instrument according to claim 1, wherein the end effector includes an electrode disposed thereon adapted for delivering electrosurgical energy to tissue.

6. A surgical instrument, comprising:
   a handle assembly supporting an actuator thereon;
   a proximal shaft member extending distally from the handle assembly and defining a longitudinal axis, the proximal shaft member including a mating portion adjacent a distal end thereof;
   a proximal drive member extending at least partially through the proximal shaft member, the proximal drive member operatively coupled to the actuator such that manipulation of the actuator induces longitudinal movement of the proximal drive member relative to the proximal shaft member, the proximal drive member including a mating portion adjacent a distal end thereof;
   an end effector configured for manipulating tissue;

a distal shaft member extending proximally from the end effector, the distal shaft member including a mating portion adjacent a proximal end thereof configured to engage the mating portion of the proximal shaft member;

a distal drive member extending at least partially through the distal shaft member, the distal drive member operatively coupled to the end effector, the distal drive member including a mating portion adjacent a proximal end thereof configured to engage the mating portion of the proximal drive member; and a knife, a distal knife rod, and a proximal knife rod, the distal knife rod operatively coupled to the knife to move the knife along the longitudinal axis, the distal knife rod and the proximal knife rod separable from each other and including mating portions;

wherein the proximal drive member is movable from an unlocked configuration where lateral engagement and disengagement of the mating portions of the shaft members and the drive members is permitted, and a locked configuration where lateral disengagement of the mating portions of the shaft members and the drive members is prohibited.

7. The surgical instrument according to claim 6, wherein the end effector includes two jaw members movable between an open configuration wherein the jaw members are substantially spaced to a closed configuration wherein the jaw members are closer together.

8. The surgical instrument according to claim 6, wherein each of the mating portions of the proximal shaft member and the distal shaft member includes a laterally prominent hook portion and a laterally indented portion for receiving the hook portion of the mating portion of the other shaft member.

9. The surgical instrument according to claim 6, wherein the actuator is operable to move the proximal drive member between the locked and unlocked configurations.

10. The surgical instrument according to claim 6, wherein the end effector includes an electrode disposed thereon adapted for delivering electrosurgical energy to tissue.

\* \* \* \* \*